(12) United States Patent
Kullik et al.

(10) Patent No.: US 8,567,389 B2
(45) Date of Patent: Oct. 29, 2013

(54) ANESTHESIA SYSTEM

(75) Inventors: Götz Kullik, Lübeck (DE); Olaf Schermeier, Lübeck (DE); Wolfgang Falb, Gross Saurau (DE); Ernst-Günther Scharmer, Krummesse (DE)

(73) Assignee: Dräger Medical GmbH, Lübeck (DE)

( * ) Notice: Subject to any disclaimer, the term of this patent is extended or adjusted under 35 U.S.C. 154(b) by 1111 days.

(21) Appl. No.: 12/527,280

(22) PCT Filed: Jan. 11, 2008

(86) PCT No.: PCT/EP2008/000157
§ 371 (c)(1),
(2), (4) Date: Aug. 14, 2009

(87) PCT Pub. No.: WO2008/116513
PCT Pub. Date: Oct. 2, 2008

(65) Prior Publication Data
US 2011/0056490 A1  Mar. 10, 2011

(30) Foreign Application Priority Data
Mar. 28, 2007 (DE) .......... 10 2007 014 838

(51) Int. Cl.
*A61M 16/00* (2006.01)

(52) U.S. Cl.
USPC ................................. 128/200.21

(58) Field of Classification Search
USPC ............ 128/200.14, 200.23, 200.24, 203.12, 128/203.15, 204.18, 204.21, 200.18, 128/200.21, 203.16, 203.26
See application file for complete search history.

(56) References Cited

U.S. PATENT DOCUMENTS

| 5,293,865 | A | 3/1994 | Altner et al. |
| 7,198,172 | B2* | 4/2007 | Harvey et al. ............... 221/8 |
| 7,997,268 | B1* | 8/2011 | Leonard et al. .......... 128/203.12 |
| 2002/0038392 | A1* | 3/2002 | De La Huerga ............ 710/8 |
| 2003/0005930 | A1* | 1/2003 | Kullik et al. ........... 128/203.25 |
| 2005/0066961 | A1* | 3/2005 | Rand .................... 128/200.14 |
| 2006/0081239 | A1* | 4/2006 | Alley et al. ............. 128/200.14 |
| 2006/0249144 | A1* | 11/2006 | DeHaan et al. .......... 128/200.14 |
| 2008/0271736 | A1* | 11/2008 | Leonard et al. ......... 128/203.12 |
| 2011/0253139 | A1* | 10/2011 | Guthrie et al. .......... 128/203.14 |
| 2012/0186581 | A1* | 7/2012 | Brauker et al. ......... 128/200.14 |

FOREIGN PATENT DOCUMENTS

EP          0 338 518 B1       10/1989

* cited by examiner

*Primary Examiner* — Lynee Anderson
*Assistant Examiner* — Bradley Philips
(74) *Attorney, Agent, or Firm* — McGlew and Tuttle, P.C.

(57) ABSTRACT

An anesthesia system is provided including an anesthesia apparatus, an anesthetic dispenser with an anesthetic reservoir, at least one dispensing parameter detection means, a contactless interface between the anesthesia apparatus and the anesthetic dispenser for transmitting data, especially the dispensing parameters, and for supplying the at least one dispensing parameter detection means with energy. The data and energy transmission takes place by means of electromagnetic field forces.

17 Claims, 2 Drawing Sheets

ANESTHESIA SYSTEM

CROSS REFERENCE TO RELATED APPLICATIONS

This application is a United States National Phase application of International Application PCT/EP2008/000157 and claims the benefit of priority under 35 U.S.C. §119 of German Patent Application DE 10 2007 014 838.2 filed Mar. 28, 2007, the entire contents of which are incorporated herein by reference.

FIELD OF THE INVENTION

The present invention pertains to an anesthesia system for providing a breathing gas enriched with anesthetic. Anesthesia systems are used in the known manner to dispense inhalation anesthetic for anesthetizing a patient during the performance of painful medical procedures.

BACKGROUND OF THE INVENTION

An anesthesia system, comprising an anesthesia apparatus and an anesthetic dispenser, in which fresh breathing gas is fed to the anesthetic dispenser via a pneumatic interface, is known from EP 0 338 518 B1. The breathing gas is enriched with anesthetic in the anesthetic dispenser at concentrations that can be set at different values. The breathing gas enriched with anesthetic returns to the anesthesia apparatus via the pneumatic interface and is fed to the patient's breathing circuit. There is no electric connection between the anesthesia apparatus and the anesthetic dispenser because of the requirements imposed in terms of safety, reliability and hygiene. The anesthetic dispenser is provided with a code for the type of anesthetic used, which code can be identified by a scanning device provided on the anesthesia apparatus in order to make information on the type of the anesthetic used available to the anesthesia apparatus. Information on the quantity of anesthetic still present is not communicated to the anesthesia apparatus. However, this information is decisive for warning the user of an insufficient quantity of anesthetic in time before or during a medical procedure. The anesthetic is checked in the line in which breathing gas enriched with anesthetic is fed to the patient. The fact that the anesthetic concentration is too low or is not present is thus determined with a time delay relative to the quantity of anesthetic actually present in an anesthetic reservoir of the anesthetic dispenser.

Information on the particular anesthetic dispensing parameters, for example, the concentration or the still available quantity in the anesthetic dispenser, is thus not available to the anesthesia apparatus or it is available only partially.

SUMMARY OF THE INVENTION

The basic object of the present invention is to improve an anesthesia system of the said type such that the communication between the anesthesia apparatus and the anesthetic dispenser is improved.

According to the invention an anesthesia system is provided comprising an anesthesia apparatus and an anesthetic dispenser with an anesthetic reservoir. At least one dispensing parameter detection means is provided. A contactless interface is provided between the anesthesia apparatus and the anesthetic dispenser for transmitting data, especially the dispensing parameters and for supplying the at least one dispensing parameter detection means with energy, wherein the data and energy transmission takes place by electromagnetic field forces.

An essential advantage of the present invention over the state of the art is that information on essential dispensing parameters, for example, the quantity of anesthetic still present, can be made available to an anesthesia apparatus with a hydraulic interface to an anesthetic dispenser, and dangerous situations for the patient are thus avoided by a corresponding control of the anesthesia apparatus.

The anesthesia system according to the present invention is preferably designed such that the anesthesia apparatus has an energy transmission antenna and the anesthetic dispenser has an energy receiving antenna for supplying a dispensing parameter detection means with energy. In addition, the anesthetic dispenser is provided with a data transmission antenna and the anesthesia apparatus with a data receiving antenna for the contactless transmission of data, especially of the dispensing parameters.

In an especially preferred embodiment of the anesthesia system according to the present invention, the at least one dispensing parameter detection means is designed as a filling level detection means for detecting the quantity of anesthetic present. The quantity of anesthetic present is detected here advantageously capacitively. A capacitive filling level detection means has a low energy consumption, so that supply via electromagnetic field forces is possible. The detected values are then in turn transmitted via electromagnetic field forces to the anesthesia apparatus and are available to this for a further control. The quantity of anesthetic can be stored in a memory of the anesthetic dispenser, transmitted directly to the anesthesia apparatus or polled by same from the memory.

In another embodiment of the anesthesia system according to the present invention, the at least one dispensing parameter detection means is designed as an angle detection means for detecting the set anesthetic concentration. The desired anesthetic concentration is set by means of a setting wheel on the anesthetic dispenser and acts as preset set point.

An anesthetic reserve that is available for a limited, short time only can be signaled to the user visually and acoustically in time with the anesthesia system according to the present invention via a display means or an alarm device on the anesthesia apparatus. Furthermore, the type of anesthetic and the concentration can be documented on the anesthesia apparatus. Patient safety is significantly increased and the operation of the anesthesia system is improved as a result.

The present invention is shown schematically in drawings 1 through 3 on the basis of exemplary embodiments and will be described in detail below with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
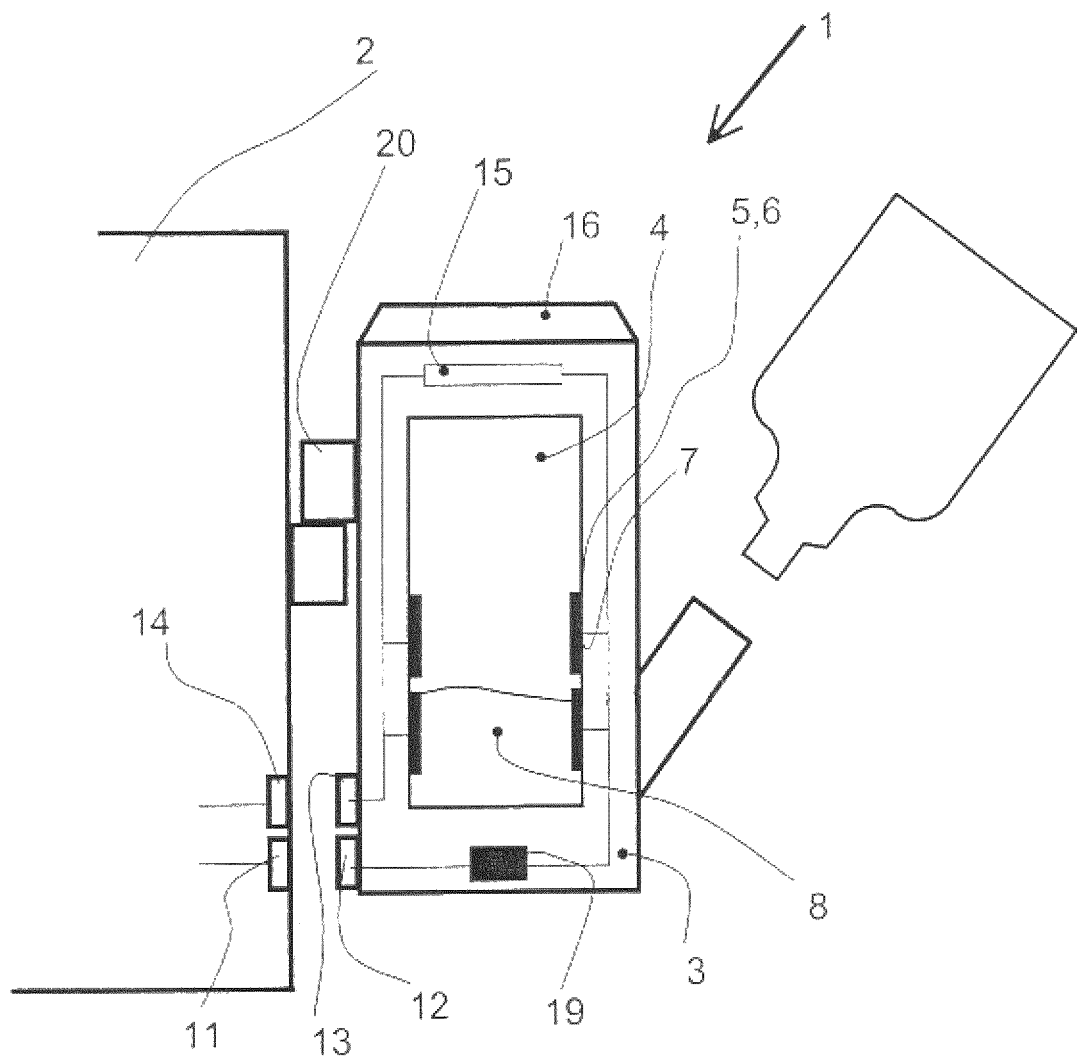
FIG. 1 is an overall view of an anesthesia system according to the present invention.

Referring to the drawings in particular, FIG. 1 shows an anesthesia system 1 according to the present invention with an anesthesia apparatus 2 and with an anesthetic dispenser 3, which are connected by means of an pneumatic interface 20 for passing through breathing gas. The anesthetic dispenser 3 comprises an anesthetic reservoir 4, in which the anesthetic 8 is stored. The anesthetic reservoir 4 is preferably made of metal. Fresh breathing gas reaches the anesthetic dispenser 3 from the anesthesia apparatus via the pneumatic interface 20. The breathing gas is enriched with anesthetic vapor in the anesthetic dispenser 3 and is again fed to the anesthesia apparatus 2 via the pneumatic interface 20. The anesthetic dispenser 3 is equipped with a dispensing parameter detection means 5, which comprises a filling level detection means 6 for detecting the quantity of anesthetic 8 present. Since the quantity of energy that can be transmitted electromagnetically for supplying the dispensing parameter detection means 5 is limited, sensors for detecting the dispensing parameters with a low energy consumption are preferably provided to guarantee their ability to function. A capacitive filling level detection means 6 is therefore especially suitable for determining the quantity of anesthetic 8 present.

Figure 2:
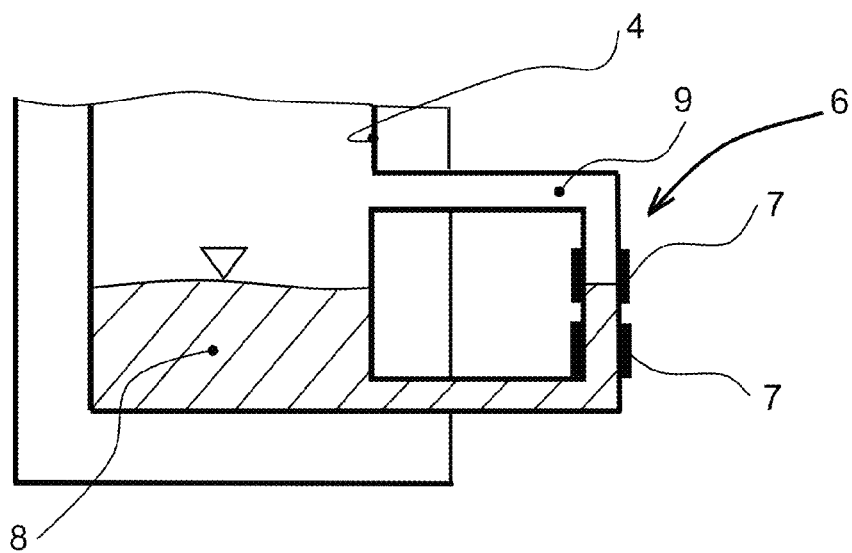
FIG. 2 is a detail view of a filling level detection means of the anesthesia system according to the present invention according to FIG. 1.

FIG. 2 shows a detail view of the filling level detection means 6. The anesthetic reservoir 4 is provided with a laterally arranged glass tube 9, which is connected to the anesthetic reservoir 4 in a lower position and in an upper position and has a viewing access to the outside in order to make possible the visual recognition of the quantity of anesthetic 8 in the anesthetic reservoir 4 for the user. The filling level detection means 6 is provided at the glass tube 9 of the anesthetic reservoir 4. The filling level detection means 6 is provided with capacitor surfaces 7, between which the anesthetic 8 is located. The anesthetic 8 acts as a dielectric here. A changing quantity of anesthetic 8 brings about a change in the quantity of dielectricity between the capacitor surfaces 7. The change in the quantity of dielectricity is an indicator of the quantity of anesthetic 8. The capacitor surfaces 7 are designed as thin metal surfaces, which are preferably applied to the surface of the glass tube 9. The capacitor surfaces 7 are preferably applied to the surface of the glass tube 9 in a ring-shaped pattern, so that visual detection of the quantity of anesthetic 8 is nevertheless possible.

As is shown in FIG. 1, an energy transmitting antenna 11, which transmits energy for supplying the filling level detection means 6 to an energy receiving antenna 12 provided in the anesthetic dispenser 3, is located at the anesthesia apparatus 2. A capacitive filling level detection means 6 has proved to be especially advantageous concerning the low energy consumption. The determined quantity of anesthetic 8 can be stored in a memory 19, transmitted directly to the anesthesia apparatus 2 or polled by the latter from the memory 19. The transmission between the anesthetic dispenser 3 and the anesthesia apparatus 2 takes place between a data transmission antenna 13 provided at the anesthetic dispenser 3 and a data receiving antenna 14 provided at the anesthesia apparatus 2. The quantity of anesthetic 8 present is thus available to the anesthesia apparatus 2 at any time. The anesthesia apparatus 2 has a display means, not shown, so that a quantity of anesthetic 8 that is available for a limited, short time only can be signaled visually at the anesthesia apparatus 2. However, it is also possible to provide an alarm device, which signals the case in which the quantity of anesthetic 8 in the anesthetic reservoir 4 drops below a defined quantity.

However, the filling level detection means 6 may also be provided in another embodiment within the anesthetic reservoir 4. The anesthetic reservoir 4 preferably consists of metal, so that the filling level detection means 6 is advantageously shielded against electromagnetic interference from the outside. The capacitor surfaces 7 are designed in the form of cylindrical surfaces as two metal tubes insulated against each other.

However, the quantity of anesthetic 8 may also be determined by the use of transponders in another embodiment variant, not shown. The filling level detection means 6 has at least two transmitting transponders for this, which are arranged in different vertical positions inside or outside the anesthetic reservoir 4 and are intended for sending signals. Another transponder is provided for receiving these signals. The receiving transponder is located in a defined position in relation to the anesthetic reservoir 4 and is used as a polling means for polling the signals of the transmitting transponders located in the different vertical positions of the anesthetic reservoir 4. Based on the anesthetic 8, the signals of the transmitting transponders are attenuated, so that only the signals that are not shielded by the anesthetic 8 are received by the receiving transponder. The quantity of anesthetic 8 present in the anesthetic reservoir 4 of the anesthetic dispenser 3 can be determined based on the number of signals received. The transponders are preferably RFID transponders. The material of the anesthetic reservoir 4 is selected to be such that it is permeable to the RF energy of the frequency range for using the communication of the RFID transponders.

Figure 3:
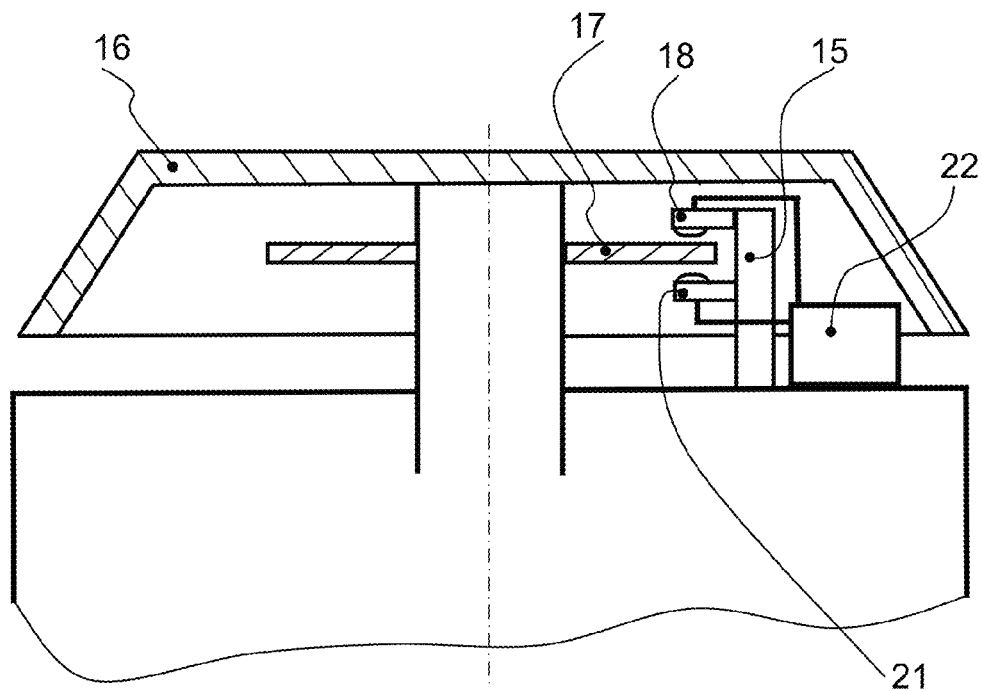
FIG. 3 is a detail view of an angle detection means of the anesthesia system according to the present invention according to FIG. 1.

FIG. 3 shows a schematic detail view of an angle detection means 15 of the anesthesia system 1 according to the present invention according to FIG. 1. The angle detection means 15 is used to detect the set concentration of the anesthetic 8 at the anesthetic dispenser 3. The concentration of the anesthetic 8 is set on the setting wheel 16 on the anesthetic dispenser 3 as desired and acts as a preset set point. An angle detection means 15 detects the setting angle of the setting wheel 16 and thus the concentration value set. The angle detection means 15 is preferably designed as an optical encoder. It is also possible to design the angle detection means 15 as a magnetic encoder. The encoder recognizes the current position of the setting wheel 16 and sends this as an electric signal. The optical encoder comprises a light-transparent film 17 provided with markings. Black lines, which are arranged at uniformly spaced locations and are arranged at right angles to the longitudinal direction of the film 17, may be provided as markings Film 17 is enclosed at least partially in a position by a photoelectric cell comprising a light transmitter 18 and a light receiver 21. A light-emitting diode may be provided as the light transmitter 18 and a phototransistor as the light receiver 21. The film 17 is connected to the setting wheel 16, so that a motion of the setting wheel 16 brings about a motion of the film 17. The light of the light transmitter 18 is shielded as a result at the markings and can be detected by the light receiver 21 between the markings only. The signals of the light receiver 21 are processed in an electronic analysis unit 22 and represent an indicator of the position of the setting wheel 16. The optical encoder is preferably arranged below the setting wheel 16, because it is protected in this position from interference effects, for example, external light. The data transmission to the anesthesia apparatus 2 takes place analogously to the transmission of the determined quantity of anesthetic 8.

Additional dispensing parameters, for example, the temperature of the anesthetic 8 in the evaporation space, can be determined with the anesthesia system 1 according to the present invention and made available to the anesthesia apparatus 2. An electric NTC element is preferably used as the temperature detection means because the energy demand of an NTC element is low and the supply can be embodied by means of the energy transmission antenna 11 and the energy receiving antenna 12.

Another dispensing parameter comprises the recognition of an inclination of the anesthesia system 1. A dispensing parameter detection means 5, not shown, for detecting the inclination of the anesthesia system 1, comprises a position detection means. The position detection means is designed as a hollow sphere with two electrodes located at mutually spaced locations in an upper area of the hollow sphere and a mercury drop in a lower area of the hollow sphere. An inclination of the anesthesia system 1 causes a motion of the mercury drop into the upper area of the hollow sphere and hence a conductive connection between the two electrodes. The connection of the electrodes can be analyzed as a signal for a corresponding inclination. Data transmission to the anesthesia apparatus 2 takes place analogously to the transmission of the above-described dispensing parameters. Visual signaling can be directly carried out on the display means of the anesthesia apparatus 2 or an acoustic alarm can be sent by means of the alarm device of the anesthesia apparatus 2.

While specific embodiments of the invention have been described in detail to illustrate the application of the principles of the invention, it will be understood that the invention may be embodied otherwise without departing from such principles.

The invention claimed is:

1. An anesthesia system, comprising:
   an anesthesia apparatus;
   an anesthetic dispenser with an anesthetic reservoir;
   at least one dispensing parameter detection means, said at least one dispensing parameter detection means comprising a filling level detection means for capacitively detecting a quantity of anesthetic present in said anesthetic dispenser, said filling level detection means comprising capacitor surfaces, between which the anesthetic is located, wherein a changing quantity of anesthetic brings about a change in a quantity of dielectricity between the capacitor surfaces, which is an indicator of the quantity of anesthetic; and
   a contactless interface between the anesthesia apparatus and the anesthetic dispenser for transmitting data, including dispensing parameters and for supplying the at least one dispensing parameter detection means with energy, wherein the data and energy transmission takes place by electromagnetic field forces.

2. An anesthesia system in accordance with claim 1, wherein the anesthesia apparatus has an energy transmitting antenna and the anesthetic dispenser has an energy receiving antenna for supplying the at least one dispensing parameter detection means with energy.

3. An anesthesia system in accordance with claim 1, wherein the anesthetic dispenser has a data transmission antenna and the anesthesia apparatus a data receiving antenna for the contactless transmission of data, especially the dispensing parameters.

4. An anesthesia system in accordance with claim 1, further comprising a memory for storing the detected dispensing parameters.

5. An anesthesia system in accordance with claim 1, further comprising a glass tube arranged laterally in relation to the anesthetic reservoir, the capacitor surfaces being designed as thin metal surfaces, which are applied preferably to a surface of the glass tube.

6. An anesthesia system in accordance with claim 1, wherein the at least one dispensing parameter detection means comprises an angle detection means for detecting a concentration of the anesthetic, which concentration is set on a setting wheel.

7. An anesthesia system in accordance with claim 6, wherein the angle detection means comprises an optical encoder.

8. An anesthesia system in accordance with claim 7, wherein the optical encoder comprises a light-transparent film provided with markings, a light transmitter and a light receiver, wherein said film is connected to the setting wheel and the light transmitter and the light receiver are arranged in relation to the film such that the light of the light transmitter is shielded at the markings and does not reach the light receiver during the motion of the setting wheel.

9. An anesthesia system in accordance with claim 1, wherein the at least one dispensing parameter detection means comprises a temperature detection means for detecting the temperature of the anesthetic.

10. An anesthesia system in accordance with claim 9, wherein the temperature detection means comprises a negative temperature coefficient (NTC) element.

11. An anesthesia system in accordance with claim 1, wherein the at least one dispensing parameter detection means comprises a position detection means for detecting an inclination of the anesthetic dispenser, the position detection means comprising a hollow sphere with at least two electrodes located at spaced locations from one another and a mercury drop, wherein the electrodes are provided in an upper area and the mercury drop in a lower area of the hollow sphere.

12. An anesthesia system in accordance with claim 4, wherein parameters of the anesthetic and of the anesthetic dispenser can be stored in the memory and polled by the anesthesia apparatus.

13. An anesthesia system in accordance with claim 1, wherein the anesthesia apparatus has at least one display means, with which the data transmitted from the anesthetic dispenser can be displayed.

14. An anesthesia system in accordance with claim 1, wherein the anesthesia apparatus has an alarm device, which signals the case in which the quantity of anesthetic in the anesthetic reservoir drops below a defined quantity.

15. An anesthesia system, comprising:
    an anesthesia apparatus;
    an anesthetic dispenser with an anesthetic reservoir;
    at least one dispensing parameter detection means comprising a position detection means for detecting an inclination of the anesthetic dispenser, said position detection means comprising a hollow sphere with at least two electrodes located at spaced locations from one another and a mercury drop, wherein the electrodes are provided in an upper area and the mercury drop in a lower area of the hollow sphere; and
    a contactless interface between the anesthesia apparatus and the anesthetic dispenser for transmitting data, including the dispensing parameters and for supplying the at least one dispensing parameter detection means with energy, wherein the data and energy transmission takes place by electromagnetic field forces.

16. An anesthesia system, comprising:
    an anesthesia apparatus;
    an anesthetic dispenser with an anesthetic reservoir;

at least one dispensing parameter detection device comprising a filling level detection device for capacitively detecting a quantity of anesthetic present in said anesthetic dispenser, said filling level detection device comprising capacitor surfaces, wherein anesthetic is located between one of said capacitor surfaces and another one of said capacitor surfaces, said filling level detection device determining the quantity of the anesthetic present in said anesthetic dispenser based on detection of changed dielectric properties between the capacitor surfaces, whereby said change in the quantity of dielectricity between the capacitor surfaces corresponds to a change in the quantity of anesthetic present in said anesthetic dispenser; and a contactless interface between the anesthesia apparatus and the anesthetic dispenser for transmitting data, including the dispensing parameters and for supplying the at least one dispensing parameter detection device with energy, wherein the data and energy transmission takes place by electromagnetic field forces.

17. An anesthesia system in accordance with claim 16, further comprising:

a glass tube arranged laterally in relation to the anesthetic reservoir, said glass tube having an glass tube interior, said glass tube interior being in communication with said anesthetic reservoir, said capacitor surfaces comprising thin metal surfaces, said thin metal surfaces engaging said glass tube, said at least one dispensing parameter detection means comprises a position detection means for detecting an inclination of the anesthetic dispenser, the position detection means comprising a hollow sphere with at least two electrodes located at spaced locations from one another and a mercury drop, wherein the electrodes are provided in an upper area and the mercury drop in a lower area of the hollow sphere.

* * * * *